United States Patent [19]
Evans et al.

[11] Patent Number: 5,523,450
[45] Date of Patent: Jun. 4, 1996

[54] CRYSTALLIZATION PROCESS FOR PREPARING GLYCEROPHOSPHOCHOLINE

[75] Inventors: Christopher T. Evans, Hertfordshire; Raymond McCague, Cambridgeshire; Nicholas D. Tyrrell, Cambridge, all of Great Britain

[73] Assignee: Genzyme Limited, England

[21] Appl. No.: 256,804

[22] PCT Filed: Dec. 31, 1992

[86] PCT No.: PCT/GB92/02408

§ 371 Date: Oct. 3, 1994

§ 102(e) Date: Oct. 3, 1994

[87] PCT Pub. No.: WO93/15088

PCT Pub. Date: Aug. 5, 1993

[30] Foreign Application Priority Data

Jan. 22, 1992 [GB] United Kingdom ............... 9201371

[51] Int. Cl.$^6$ ........................................... C07F 9/10
[52] U.S. Cl. .................................. 558/146; 558/169
[58] Field of Search ................................. 558/146

[56] References Cited

FOREIGN PATENT DOCUMENTS 9013552 11/1990 European Pat. Off. .

OTHER PUBLICATIONS

Brockerhoff, H. et al. (1965) "Simplified Preparation of L–a–Glyceryl Phosphoryl Choline" *Canadian Journal of Biochemistry*, 43: 977.

Tattrie, N. et la. (1958) "L–a–Glycerophosphorylcholine" *Biochemical Preparations*, 6:16–19.

Hanahan, D. et la. (1952) "L–a–Glycerophosphorylcholine" *Biochemical Preparations*, 9:55–58.

*Primary Examiner*—Johann Richter
*Assistant Examiner*—Michael G. Ambrose
*Attorney, Agent, or Firm*—William G. Gosz

[57] ABSTRACT

A process for preparing substantially dry GPC (glycerophosphocholine in enantiomeric form) from wet GPC without racemisation, comprises subjecting the wet GPC to reduced pressure and elevated temperature, to reduce the water content and give highly viscous GPC; adding ethanol or another suitable solvent and crystallising GPC therefore with cooling; filtering the crystalline GPC and removing solvent therefrom under reduced pressure; characterised in that the elevated temperature is at least 45° C.; and the solvent is added to the highly viscous GPC. This process produces an apparently new form of L-α-Glycerophosphocholine, m.p. 148°–152° C.

1 Claim, No Drawings

CRYSTALLIZATION PROCESS FOR PREPARING GLYCEROPHOSPHOCHOLINE

This application was filed under 35 U.S.C. 371 and was based upon PCT International Application No. PCT/GB92/02408 which was filed on Dec. 31, 1992.

This invention relates to a process for preparing substantially dry GPC, i.e. glycerophosphocholine, in enantiomeric form.

GPC is a valuable material, e.g. as an intermediate in the preparation of pharmaceutical-grade phospholipids. For this purpose, it is required in anhydrous form, but it is then extremely hygroscopic. While various methods are known for obtaining dry GPC, there is no published process which is operable on a commercial scale.

Hanahan, Biochem. Prep. 9 (1952) 55, describes the preparation of GPC as its cadmium chloride complex, following the deacylation of lecithin with alkaline hydroxylamine, followed by neutralisation and extraction. Tattrie et al, Biochem. Prep. 6 (1958) 16–19, describe liberation of free GPC from the cadmium chloride complex and subjection to reduced pressure and elevated temperature, to reduce the water content and give highly viscous GPC, at a bath temperature of 45° C.; drying the syrup under reduced pressure over $P_2O_5$; dissolving the vitreous product in ethanol and crystallising GPC therefrom with cooling; and filtering the crystalline GPC, washing with ethanol and then ether and removing solvent therefrom under reduced pressure. The product is described as follows: "L-α-Glycerophosphorylcholine is a white crystalline compound melting at 142.5°–143° with sintering at 141° . The crystalline diester is extremely hygroscopic." It is reported that "the checkers were unable to obtain a crystalline product".

Brockerhoff et al, Can. J. Biochem. 43 (1955) 1777, describe obtaining GPC from egg yolk lipids by precipitation with acetone, removal of acidic phospholipids over $Al_2O_3$, dissolution in ether and the addition of aqueous methanolic tetrabutylammonium hydroxide. The precipitate of GPC was dissolved in methanol, re-precipitated with ether and held over $P_2O_5$: "The analyses indicated that the GPC contained 1 mole of water."

A practical method for drying GPC has now been found; the process has similarities to that described by Tattrie et al., but does not require the use of the cadmium chloride complex as starting material, employs a somewhat higher temperature in the first stage of water removal, e.g. 45°, 50°, 55° C. or higher, and utilises anhydrous ethanol or another suitable solvent directly on the highly viscous GPC. Inter alia, it has been found that the use of phosphorus pentoxide is unnecessary.

Without wishing to be bound by theory, one reason for the greater practicability of the novel process may be more efficient first-stage drying, with a consequent greater difference between that temperature and the relatively cool temperature required for crystallisation (it is of course important that the temperature, or any other condition, should not be such that the enantiomeric form of the GPC is lost). The consequence of the novel process is a useful and apparently novel form of GPC, i.e. L-α-glycerophosphocholine, m.p. 152° C. Further, it appears that, during the process, a novel alcoholate or solvate of GPC is obtained, in crystalline form.

The following Example illustrates the invention.

EXAMPLE

A 50 jacketed glass vessel with a lid and a glycol-cooled condenser is charged with between 5 and 10 kg wet GPC (water content 10–20%). The vessel is sealed and the contents are stirred at 50 rpm for about 30 min, at a jacket temperature of 65°–70° C. A vacuum pump is connected, and the pressure in the vessel reduced to approx. 0.1 torr.

As the system pressure falls, the contents of the vessel begin to boil. Water vapour condenses out and the volume of distillate is monitored. The pump is operated so as to avoid exceeding the capacity of the condenser, whilst maintaining a steady boil-up rate.

The temperature is monitored, maintaining the GPC at above 55° C. to avoid premature crystallisation. Water removal proceeds smoothly over 2–3 h, leaving a clear, bright, glassy syrup. The water content of this highly viscous material is about 4%. This point may be controlled by advance calculation of the target distillate volume to 4% moisture, given the amount and water content of the residual starting material.

The vessel is then charged with 2.0 l ethanol per kg of 15% wet weight GPC. To aid dissolution, 25% of the total volume of ethanol is charged and mixed thoroughly before the remainder is added. Heating is continued, to achieve a batch temperature of about 65° C. and dissolve the products of any premature crystallisation. An almost clear solution is obtained (some residual solids are acceptable).

The contents of the vessel are now reduced in temperature, with an initial jacket temperature set point of 50° C. The batch temperature is monitored and the jacket temperature continuously reduced, at about 20° C. below the batch temperature, until the latter reaches approx. 5° C. As the batch temperature falls, GPC crystallises (possibly in the form of the alcoholate) from solution, giving a thick slurry, A stirrer speed of 30 rpm or more keeps this adequately suspended. If no crystals form, seeding may be necessary. To complete crystallisation, the temperature of the mixture is maintained at below 10° C. for 30 min.

The stirrer is stopped and, before the slurry settles, it is drawn from the vessel under vacuum via a header vessel and transferred to a Hathenware filter in portions of about 10 l slurry, such that the product is comfortably accommodated within the filter. Vacuum is applied to the filter system until most of the mother liquor has been drawn off. During filtration, steps are taken to exclude atmospheric moisture.

The vessel is charged with 1 l ethanol per kg of wet GPC, and chilled to a temperature of about 5° C. The chilled ethanol is transferred to the filter via the header vessel, again taking steps to exclude atmospheric moisture. The ethanol is mixed with the filtered crystals and vacuum is applied to draw off the ethanol wash. The washing procedure is repeated once.

At this stage, the crystals may be transferred to a container which is flooded with argon and then sealed, prior to vacuum-drying. Vacuum-drying initially comprises the use of a water aspirator and a water bath at 40°–50° C. Solvent distils off over 2–3 h. After distillation, a rotary vane vacuum pump is substituted for the aspirator and the temperature of the water bath raised to 60° C., to complete the drying process.

The melting point of the product is 148°–152° C. The yield is typically 85% on a dry weight basis for GPC.

In order to pack the product, the vacuum is released with argon. After reducing the temperature of the flask to a comfortable handling temperature, the product is packed into a weighed polythene sack which is sealed in an airtight container.

Further product may be obtained by concentrating the liquors and washes from several preparations as above, then repeating this procedure on the GPC thus recovered.

We claim:

1. A process for preparing substantially dry GPC from wet GPC without racemisation, said process consisting essentially of the steps of:

subjecting the wet GPC to reduced pressure and an elevated temperature of at least 45° C. to reduce the water content and give highly viscous GPC;

adding ethanol directly to the highly viscous GPC to form a solution, and cooling the solution to crystallize the GPC;

filtering the crystallized GPC; and removing solvent from the GPC under reduced pressure to recover dry GPC.

* * * * *